United States Patent [19]
Watanabe et al.

[11] Patent Number: 5,735,078
[45] Date of Patent: Apr. 7, 1998

[54] METHOD OF PRODUCING INTERGENERIC OR INTERSPECIFIC HYBRIDS BY ION BEAM IRRADIATION

[75] Inventors: Hiroshi Watanabe; Atsushi Tanaka, both of Gunma-ken; Shigemitsu Tano, Chiba-ken; Masayoshi Inoue, Kyoto; Takao Yamashita, Osaka; Akio Nakamura, Shiga-ken, all of Japan

[73] Assignee: Japan Atomic Energy Research Institute, Tokyo, Japan

[21] Appl. No.: 790,733

[22] Filed: Jan. 27, 1997

[30] Foreign Application Priority Data

Feb. 19, 1996 [JP] Japan ..................................... 8-030435

[51] Int. Cl.⁶ .............................. A01B 79/00; A01C 1/00; A01G 7/04; A01H 1/02
[52] U.S. Cl. ........................ 47/58; 47/1.41; 47/DIG. 1; 47/DIG. 8
[58] Field of Search ........................ 47/58, 1.41, DIG. 1, 47/DIG. 8

[56] References Cited

PUBLICATIONS

Cornu et al.; Petunia, A Biological Model—Application to the Study and the Use of the Genetic Potential of Pollen; Bulletin De La Societe Botanique De France—Actualites Botaniques; 1990, 137(2), 41–48 (Abstract Only).

Hasegawa et al.; Effects of Gamma–Ray Irradiation on Cultured Anthers of Tobacco (*Nicotiana tabacum* L.). Radiosensitivity and Morphological Variants Appearing in the Haploid Plants; Skokubutsu Soshiki Baiyo (1995), 12(3), 281–287 (Abstract Only).

*Primary Examiner*—David T. Fox
*Assistant Examiner*—Kent L. Bell
*Attorney, Agent, or Firm*—Banner & Witcoff, Ltd.

[57] ABSTRACT

Plants of different genera or species are crossed after either pollen, anther or pistil is irradiated with an ion beam of a proton or an element up to uranium which have a LET of 5–10,000 keV/μm and are applied in a dose range of 1–2,000 Gy.

1 Claim, No Drawings

METHOD OF PRODUCING INTERGENERIC OR INTERSPECIFIC HYBRIDS BY ION BEAM IRRADIATION

BACKGROUND OF THE INVENTION

This invention relates to a method of producing intergeneric or interspecific hybrids in plants which are irradiated with an ion beam on pollen, anther or pistil so as to overcome cross incompatibility.

Interspecific or intergeneric crossing of plants has heretofore been conducted in various ways with a view to introducing into a target species or genus a gene or genes found in other species or genus irrespective of whether they are closely or distantly related. However, fertilization often fails due to such factors as the failure of pollen to germinate or obstruction of the elongation of pollen tubes; even if fertilization occurs, seeds may not be obtained due to the overcoming or insufficient growth of the fertilized embryo; even if seeds are obtained, they may not germinate; even if the seeds germinate, they may die before growing into maturity. Thus, it has been extremely difficult or even impossible to obtain interspecific or intergeneric hybrids of plants on account of the incompatibility for crossing due to the reproductive isolation mechanism the plants have acquired in the process of their evolution.

Various treatments have hitherto been made to overcome the incompatibility for the crossing of plants and they include: (1) increasing the number of crossings, or attempting reciprocal or bridge-crossing, or trying to perform crossing after doubling the chromosomes in one or both parents; (2) treating with hormones such as auxins and gibberellins during pollination; (3) growing the embryo, ovule or ovary of a plant after fertilization; (4) producing redifferentiated individuals by cell fusion; and (5) applying γ-rays or X-rays to the bud, ovary, style or pollen on a plant either before or after crossing.

The first method is a classical approach which aims at finding a desired hybrid that is obtainable at an extremely low frequency but this requires huge manpower and time. The second method is intended to accelerate the development of the fertilized embryo in a specific way by hormone treatment but; however, in the absence of any definite criteria for the type and concentration of the hormone to be used and with many points left unknown, it is difficult to determine optimal conditions. The third method is an attempt to save the embryo of the hybrid by artificial cultivation before its abortion but this is not applicable to hybrids which have not been established in terms of culture conditions and, what is more, high-volume treatment is difficult to achieve since great skill is required to implement the method. The fourth method is an entirely new approach that is capable of yielding not only interspecific but also intergeneric hybrids but there are many conditions that need be established in various processes including the isolation of a protoplast, its cultivation, selection and redifferentiation and it is often difficult to establish those conditions. In addition, an inevitable problem exists in that the mutation or loss of chromosomes or genes is liable to occur in the process of cultivation which progresses under a dedifferentiated state. The fifth method intends to increase the frequency of hybrid formation by radiation treatment and it features relative ease in operation; yet, depending on the irradiation dose, the characteristics of the desired hybrid may vary considerably due to mutation.

The radiation treatment method described above is fairly simple in operation since it is identical to ordinary crossing except that the whole plant body or its partial areas or components such as bud, style and pollen are irradiated. If the irradiated pollen is to be used in crossing, it can be collected in a large quantity and yet a small amount of the pollen suffices for pollination; hence, various types of mother plant may be pollinated to yield hybrids in a great number of crossing combinations. In the artificial culture and cell fusion methods, it is very difficult to establish a desired culture line and these methods are only applicable to limited lines. In contrast, the radiation treatment method has the advantage of being applicable to various plants.

However, low-LET (linear energy transfer) radiations such as γ- and X-rays that are used in the conventional practice of the radiation treatment method cannot be applied to specified sites and considerable difficulty has been encountered in determining appropriate doses for hybrid production. In addition, if those radiations are applied at sufficient doses to overcome the incompatibility of plants for crossing, mutation will occur in several genes, making it difficult to yield a hybrid that is the correct inheritor of the genes in both parents. At low irradiation doses, the mutation problem can be controlled but, on the other hand, the effectiveness of the applied radiation in overcoming the incompatibility of plants for crossing is so small that the desired hybrid cannot be produced in high efficiency.

SUMMARY OF THE INVENTION

The present invention has been accomplished under these circumstances and has as an object providing a method of producing an integral hybrid efficiently from plants which are exposed to an ion beam of high LET to overcome their incompatibility for crossing of parent without causing any mutation in a desired gene or genes.

With a view to attaining this object, the present inventors substituted an ion beam of high LET for the conventionally used low-LET radiations such as γ- and X-rays and found that an integral hybrid could be produced efficiently. The method of the invention for producing hybrids after ion beam irradiation is advantageous in that it is capable of acquiring the desired hybrid more efficiently than the prior art method using γ- and X-rays and that the hybrid thus produced is the correct inheritor of the genes in both parents.

DETAILED DESCRIPTION OF THE INVENTION

The ion beam to be used in the present invention means a beam produced by accelerating the ion of a proton or an element in the group of elements up to uranium that can be accelerated by means of the currently available accelerators. The beam energy should be selected in accordance with the size of the target to be irradiated. If the anther, bud, ovary, style or other part of a plant is to be directly irradiated as they remain attached on the plant body, the size of the target to be irradiated is measured preliminarily and an ion beam having the corresponding range may be applied to provide a satisfactory result.

The most convenient way is to perform pollination after pollen is taken out of the anther and exposed to an ion beam; in this case, too, applying an ion beam appropriate for the depth of the target such as the cytoplasm or nucleus is necessary to ensure the intended result. If the removed pollen can withstand vacuum, it may be irradiated with an ion beam within a vacuum enclosure; normally, the ion beam is drawn out of the vacuum enclosure and applied to the target.

The required irradiation dose is determined by the radiation sensitivity of the target. If pollen is to be irradiated, an optimal dose must be determined on the basis of a preliminary experiment in which the pollen is subjected to irradiation in a dry state. If the target remains attached on the plant body, it is normally more sensitive to radiations than when it is in a dry state and an appropriate dose is desirably determined from the range of 1–100 Gy.

The biological action of ion beams includes killing and mutagenic effects which are known to be several to several tens of times higher than those of low-LET radiations such as γ- and X-rays. This is because the energy of ion beams is concentrated in local areas of cells or tissues, thereby causing great damage to the DNA. Suppose that an X-ray having a LET of 1 keV/μm and an ion beam having a LET of 10 keV/μm are each applied to a single cell at the same dose; then, an energy that is imparted by a single ion beam corresponds to the energy of 100 X-rays. Since a single ion beam is sufficient to impart a practically destructive quantity of energy to a local area, it will exert a substantial effect on organisms. In addition, the localized application of the energy limits the radiation damage to a specified site of the cell and the integrity of the other sites is maintained with the potential auxiliary effects being reduced. This is why ion beams as employed to overcome the incompatibility of plants for crossing will yield more integral hybrids than low-LET radiations such as γ- and X-rays.

If cells are exposed to γ-rays and other low-LET radiations in necessary doses to overcome their incompatibility or crossing, the irradiation is uniform enough to induce occasional mutation as an ancillary effect, making it difficult to obtain a hybrid that is the correct inheritor of the genes in both parents. On the other hand, integral hybrids can be obtained in high yield by irradiation with ion beams because only the target that is the potential cause of the cross incompatibility can be destroyed more efficiently than in the case of exposure to γ-rays and other low-LET radiations.

The ion beams may have LET values in the range of 5–10,000 keV/μm, with 5–300 keV/μm being most effective on the normal target. With increased LETs, a greater energy will be imparted by a single ion to thereby increase the chance of local damage to take place.

While various combinations exist for crossing, hybrids produced by crossing between the distantly related have such general characteristics that seeds may not be formed by interspecific or intergeneric hybrids even if they are obtained by crossing after irradiation with an ion beam. In general, the sterility of the hybrid is due to the cytological disturbance and such sterile hybrids can be made reproductive to form seeds by performing chromosomal doubling with colchicine or other suitable agents to form amphidiploids. Even the hybrids obtained by crossing after ion beam irradiation may be treated by the same method to become reproductive (i.e., capable of forming seeds) to achieve smooth growth of following generations.

The following examples are provided for the purpose of further illustrating the present invention. It should be noted that the scope of the invention which, in principle, is based on the action of ion beams is by no means limited by those examples.

EXAMPLE 1

The samples to be crossed were tobacco cultivar, *Nicotiana tabacum* L. var. BY-4 and wild tobacco species *Nicotiana gossei* Domin. If the wild species is the mother to be crossed with the cultivar, seeds will normally occur and germinate but the seedling will turn brown at the stage where a cotyledon develops; the brown seedling will eventually die and it is practically impossible to obtain a mature plant.

In order to investigate the effect of ion beam irradiation on the overcoming of the incompatibility for crossing, fully ripened pollen on the cultivar *N. tabacum* was irradiated with 6 MeV of He$^{2+}$ ions and thereafter applied to the wild species *N. gossei*. The percentages of fertile seed capsule formation, seed germination and plant survival were compared with the data obtained by exposure to γ-rays. The results are shown in Table 1 below.

TABLE 1

Effect of Irradiation of *N. tabacum* Pollen in the Crossing of *N. gossei* × *N. tabacum*

| Radiation | Dose, Gy | Fertile Seed Capsule Formation, % | Germination, % | Survival, % |
|---|---|---|---|---|
| Unirradiated | 0 | 66.7 | 76.7 | 0 |
| He$^{+2}$ ion beam | 400 | 5.4 | 93.3 | 1.8 |
|  | 800 | 2.3 | 92.5 | 5.4 |
|  | 1200 | 0 | 0 | 0 |
| γ-ray | 50 | 54.6 | 4.2 | 0.1 |
|  | 100 | 20.0 | 3.7 | 0.5 |
|  | 200 | 16.4 | 1.8 | 0.4 |

When unirradiated pollen was used in the crossing of *N. gossei*×*N. tabacum*, fertile seed capsules were produced and the seeds germinated well but all of them died during the seedling stage.

When the γ-rays treated pollen was used, the percentage of fertile seed capsule formation decreased with the dose; in addition, the percentage of seed germination dropped markedly compared to the result with the unirradiated pollen, and the percent survival of the hybrid plants was also very low. As a consequence, the percent acquisition of the mature hybrid plants was only 3.7×10$^{-5}$.

When the He$^{2+}$ ion irradiated pollen was used, the percentage of fertile seed capsules also decreased but the percentage of seed germinated was higher than when the unirradiated pollen was used whereas the percent survival of the hybrid plants was higher than when the γ-ray treated pollen was used. As a result, the percent acquisition of mature hybrid plants was 1.1×10$^{-3}$, which was about 30 times as high as when the γ-ray treated pollen was used. This obviously shows that the ion beam irradiation caused a different effect on pollen than the γ-ray irradiation.

In the case of γ-ray irradiation, the percent germination dropped so appreciably that it may have caused other effects than the overcoming of the cross incompatibility, as typified by the induction of chromosomal aberrations and mutation. In contrast, the ion beam irradiation would be specifically effective in overcoming the incompatibility for crossing in view of the extremely high percentage of germination despite the drop in the percentage of fertile seed capsules.

EXAMPLE 2

As in Example 1, cultivar *N. tabacum* was crossed with wild species *N. gossei* and the effect of ion beam irradiation on the percent survival of hybrid seedlings was investigated as a function of LET. Fully ripened pollen on the cultivar was irradiated with an ion beam at varying LET levels and applied to the wild species *N. gossei*. The percentage of germination of the resulting seeds and the percent survival of the seedlings are shown in Table 2.

The irradiation dose was held constant at 800 Gy while the LET was varied over the range from 15 to 1,800 keV/μm. The percentage of seed germination had a tendency to decrease with the increasing depth of ion beam implantation but no definite LET dependency was observed. On the other hand, the percent survival of the seedlings reached a maximum at about 150 keV/μm. From the data shown in Table 2, one can see that in ion beam irradiation, about 1% survival could be attained even at low LET levels and the survival percentage of seedlings could be further increased by selecting an optimal LET level. The increased percentage of seedlings survival is a necessary condition for acquiring a large number of mature hybrid plants and it will increase the potential for selecting integral hybrids after the irradiation.

TABLE 2

LET Dependency of the Effect of Ion Beam
Irradiation on the Percentage of Germination
of Hybrid Seeds and the Percent Survival of Seedlings

| Ion species | Range, μm | LET, keV/μm | Germination, % | Survival, % |
|---|---|---|---|---|
| $He^{+2}$ | 1700 | 15 | 11.5 | 1.6 |
|  | 250 | 70 | 80.8 | 2.3 |
|  | 30 | 150 | 92.5 | 5.4 |
| $C^{5+}$ | 1100 | 110 | 33.4 | 2.7 |
| $Ne^{7+}$ | 330 | 550 | 78.0 | 1.8 |
| $Ar^{13+}$ | 120 | 1800 | 88.1 | 1.2 |

EXAMPLE 3

Mature hybrids were produced after irradiation with γ-rays and high-LET (150 keV/μm) $He^{2+}$ ion beams. A comparison of the morphological characteristics of the hybrids is shown in Table 3 below.

TABLE 3

Morphologies of Hybrids Obtained After
Irradiation with Ion Beams or Gamma-Rays

| Character | N. gossei | Hybrid/ion beam | Hybrid/γ-ray | N. tabacum |
|---|---|---|---|---|
| <<Flower>> | | | | |
| Color | white | pale pink | pink stripes in white background | dark pink |
| Shape of petal | star-shaped | star-shaped | star-shaped | star-shaped |
| Shape of petal tip | round | pointed | pointed | pointed |
| Warpage of petal | − | + | + | ++ |
| Twisting of calyx | no | no | yes | no |
| Density of trichomes | High | Moderate | Moderate | Low |
| <<Leaf>> | | | | |
| Leaf shape | spatulate | prolate elliptic | lanceolate | elliptic |
| Shape of leaf tip | round | pointed | pointed | pointed |
| Leaf margin | smooth | smooth | wavy | smooth |
| Folds in the petiole | + | + | − | − |
| Petiole | − | − | (+) | (+) |

As Table 3 shows, most of the hybrids obtained after ion beam irradiation had characters intermediate between those of the wild species and the cultivar as represented by the color of flower and the number of trichomes. As for the other characters, the hybrids were inheritors to either parent.

In contrast, the hybrids obtained after irradiation with γ-rays were not only inheritors to either parent but they also exhibited characters found in neither parent, such as the twisting of calyx and a wavy (sawtoothed) rather than smooth leaf margin. This shows that the overcoming of the cross incompatibility was not the only result obtainable by exposed to γ-rays, but chromosomal aberrations and various forms of mutations occurred in the hybrids.

In contrast, the hybrids obtained after the ion beam irradiation had none of the characters non-existent in the parents but only the effective overcoming of the cross incompatibility occurred. This is characteristic of the overcoming of the cross incompatibility that could be accomplished by ion beam irradiation. One can therefore conclude that the irradiation with ion beams is a very advantageous and effective means of introducing genes in a wild plant species into a cultivar.

EXAMPLE 4

Wild species have various kinds of potent resistant genes to pests and insects but cultivars have very few those genes. Therefore, the protocol in Example 3 was modified such that a resistance test was conducted in order to see how the resistance of N. gossei to tobacco green peach aphid (Myzus persicae SULZER) was introduced into the hybrids obtained after irradiation with ion beams or γ-rays. The results are shown in Table 4 below.

TABLE 4

Resistance to Green Peach Aphid of
the Hybrids Obtained After Exposure to
Radiations and Their Parents

| Species | Days of Aphid Survival | | Percent Survival at 10 Days |
|---|---|---|---|
|  | Average | Maximum |  |
| N. gossei | 1 | 1 | 0 |
| Hybrid/ion beam | 2.5 | 3 | 0 |
| Hybrid/γ-ray | 3.7 | 4 | 0 |
| N. tabacum | ≧10 | ≧10 | 100 |

As is clear from Table 4, aphids could survive on the Wild species N. gossei for only one day after the inoculation and they all died on the second day of the inoculation. In contrast, no aphids would die on the cultivar, N. tabacum, and all of the aphids tested continued to grow by molting even at 10 days after the inoculation. On the hybrids obtained after ion beam irradiation, the aphids could survive for only 3 or 4 days and they all died thereafter. This obviously shows the successful introduction of the resistant gene applied in *N. gossei* into the hybrids.

According to the present invention, if plants are irradiated with an ion beam under the conditions stated herein, one only need perform artificial crossing by the conventional procedure to accomplish efficient production of integral interspecific or intergeneric hybrids from various combinations of close or remote relatives, into which a resistant gene against pests and insects and other useful genes for cultivation have been successfully introduced.

What is claimed is:

1. A method of producing an integral interspecific or intergenetic hybrid into which a gene providing resistance to pests and insects has been introduced, said method comprising crossing tobacco cultivar with wild tobacco species after irradiating pollen or anther of the tobacco cultivar with an ion beam in a dose range of between about 1 and 2000 Gy of an ion beam of H, He, C, N, O, Ne, Ar, Kr, or Xe which has an LET of between about 5 and 10,000 Kev/μm.

* * * * *

UNITED STATES PATENT AND TRADEMARK OFFICE
CERTIFICATE OF CORRECTION

PATENT : 5,735,078

DATED : April 7, 1998

INVENTOR(S): Hiroshi Watanabe, et al.

It is certified that error appears in the above-identified patent and that said Letters Patent is hereby corrected as shown below:

Column 4, delete lines 1-16, (Table 1) and insert the following:

Table 1

Effect of Irradiation of *N. tabacum* Pollen in the Crossing of *N. gossei* × *N. tabacum*

| Radiation | Dose, Gy | Fertile Seed Capsule Formation, % | Germination, % | Survival, % |
|---|---|---|---|---|
| Unirradiated | 0 | 66.7 | 76.7 | 0 |
| He$^{+2}$ ion beam | 400 | 5.4 | 93.3 | 1.8 |
|  | 800 | 2.3 | 92.5 | 5.4 |
|  | 1200 | 0 | 0 | 0 |
| γ-ray | 50 | 54.6 | 4.2 | 0.1 |
|  | 100 | 20.0 | 3.7 | 0.5 |
|  | 200 | 16.4 | 1.8 | 0.4 |

Signed and Sealed this

Twenty-fifth Day of July, 2000

Attest:

Q. TODD DICKINSON

*Attesting Officer*     *Director of Patents and Trademarks*